(12) United States Patent
Oeschger

(10) Patent No.: US 6,449,566 B1
(45) Date of Patent: Sep. 10, 2002

(54) ACOUSTIC SCATTERING MEASUREMENT AND PROCESSING FOR DETERMINING VARIANCES IN MULTIPLE FEATURES

(75) Inventor: John Oeschger, Panama City Beach, FL (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 104 days.

(21) Appl. No.: 09/706,549

(22) Filed: Nov. 6, 2000

(51) Int. Cl.$^7$ .............................................. G01F 17/00
(52) U.S. Cl. ...................... 702/54; 702/50; 73/633; 367/131; 367/173; 342/22
(58) Field of Search ....................... 702/50, 54; 73/633; 367/173, 131; 342/22

(56) References Cited

U.S. PATENT DOCUMENTS

| | | | | |
|---|---|---|---|---|
| 3,903,520 A | * | 9/1975 | Shostak | 340/850 |
| 5,642,331 A | * | 6/1997 | Medeiros et al. | 367/13 |
| 5,666,327 A | * | 9/1997 | Medeiros et al. | 367/131 |
| 6,216,540 B1 | * | 4/2001 | Nelson et al. | 73/633 |

* cited by examiner

Primary Examiner—John S. Hilten
Assistant Examiner—Stephen J. Cherry
(74) Attorney, Agent, or Firm—Harvey A. Gilbert; Donald G. Peck

(57) ABSTRACT

A method is provided for determining multiple feature variances in a medium. Acoustic sources are positioned on one side of a selected scattering direction. Acoustic receivers are positioned on an opposite side of the selected scattering direction such that, for each acoustic source, there is a corresponding acoustic receiver located at a mirror-imaged position relative to the selected scattering direction, and such that a Bragg scattering wave vector associated with each acoustic source/receiver pair is parallel to the selected scattering direction. Each acoustic source is operated at a unique time to direct a broadband ultrasonic pulse at the region of interest. An acoustic scattered wave reflects from the region of interest and is detected as a waveform at the pair's acoustic receiver. Each waveform is converted to the frequency domain to form a spectral waveform. A band of Bragg wave numbers is determined for each spectral waveform. Variations in multiple features of the medium are then determined by solving a complex acoustic scatter relationship as a function of the band of Bragg wave numbers associated with the particular source/receiver pair.

16 Claims, 2 Drawing Sheets

US 6,449,566 B1

ACOUSTIC SCATTERING MEASUREMENT AND PROCESSING FOR DETERMINING VARIANCES IN MULTIPLE FEATURES

ORIGIN OF THE INVENTION

The invention described herein was made in the performance of official duties by an employee of the Department of the Navy and may be manufactured, used, licensed by or for the Government for any governmental purpose without payment of any royalties thereon.

FIELD OF THE INVENTION

The invention relates generally to acoustic processing, and more particularly to a method and system for making acoustic scattering measurements in a medium and processing same in order to determine variances in multiple features of the medium.

BACKGROUND OF THE INVENTION

Measurements of features of a medium are typically accomplished with sensors placed in the medium. For example, oceanographers often place sensors in the water to record time-changing features such as temperature, salinity, etc. This requires the invasive placement of a sensor(s) in the medium of interest. Such placement is time consuming and can disrupt the medium in the region of interest.

SUMMARY OF THE INVENTION

Accordingly, it is an object of the present invention to provide a method and system for making non-invasive measurements of one or more of a medium's features.

Another object of the present invention is to provide a method and system for making non-invasive acoustic measurements and processing same in order to determine variances in one or more features of a media.

Still another object of the present invention is to provide a method and system for using acoustic scattering measurement techniques and for processing of such measurements to determine variances in multiple features of a medium.

Yet another object of the present invention is to provide a method and system for using acoustic scattering measurement techniques and for processing of such measurements to determine variances in water temperature and salinity.

A further object of the present invention is to provide a method and system for using acoustic scattering measurement techniques and for processing of such measurements to determine variances in sound speed and density of human tissue.

Other objects and advantages of the present invention will become more obvious hereinafter in the specification and drawings.

In accordance with the present invention, a method is provided for determining multiple feature variances in a medium. A scattering direction is selected relative to a region of interest in a medium. Acoustic sources are positioned on one side of the selected scattering direction. Acoustic receivers are positioned on an opposite side of the selected scattering direction such that, for each acoustic source, there is a corresponding acoustic receiver located at a mirror-imaged position relative to the selected scattering direction. As a result, a Bragg scattering wave vector associated with each acoustic source/receiver pair is parallel to the selected scattering direction. Each acoustic source is operated at a unique time to direct a broadband ultrasonic pulse at the region of interest. An acoustic scattered wave reflecting from the region of interest is detected as a waveform at the acoustic receiver that corresponds to the acoustic source that emitted the broadband ultrasonic pulse. Each waveform is digitized and then converted to the frequency domain to form a spectral waveform. A band of Bragg wave numbers is determined for each spectral waveform. Variations in multiple features of the medium are then determined by solving a complex acoustic scatter relationship as a function of the band of Bragg wave numbers associated with the particular source/receiver pair.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

The present invention exploits the behavior of a sound wave in a medium to determine variances in multiple features of the medium. As is known in the art, whenever a traveling sound wave encounters a region of certain singular or multiple features, the behavior of the sound wave is altered. The medium's features will cause some of the energy of the sound wave to travel or scatter in directions other than its original motion and is, therefore, generally referred to as the scattered wave. The scattered wave inherently contains information pertaining to the feature that caused the original sound wave to scatter. Because of the finite temporal extent of the original sound wave, the information (bandwidth) that can be obtained by the scattered wave on a feature is similarly finite. One way the amount of information on a feature can be expanded is by scattering from the feature using different scattering angles. When a single feature is responsible for the scattered wave, it is trivial to obtain the desired information on the feature. However, when there are multiple features responsible for the scattering, the problem of feature extraction has been difficult or impossible. The present invention addresses this multiple feature extraction problem.

Figure 1:
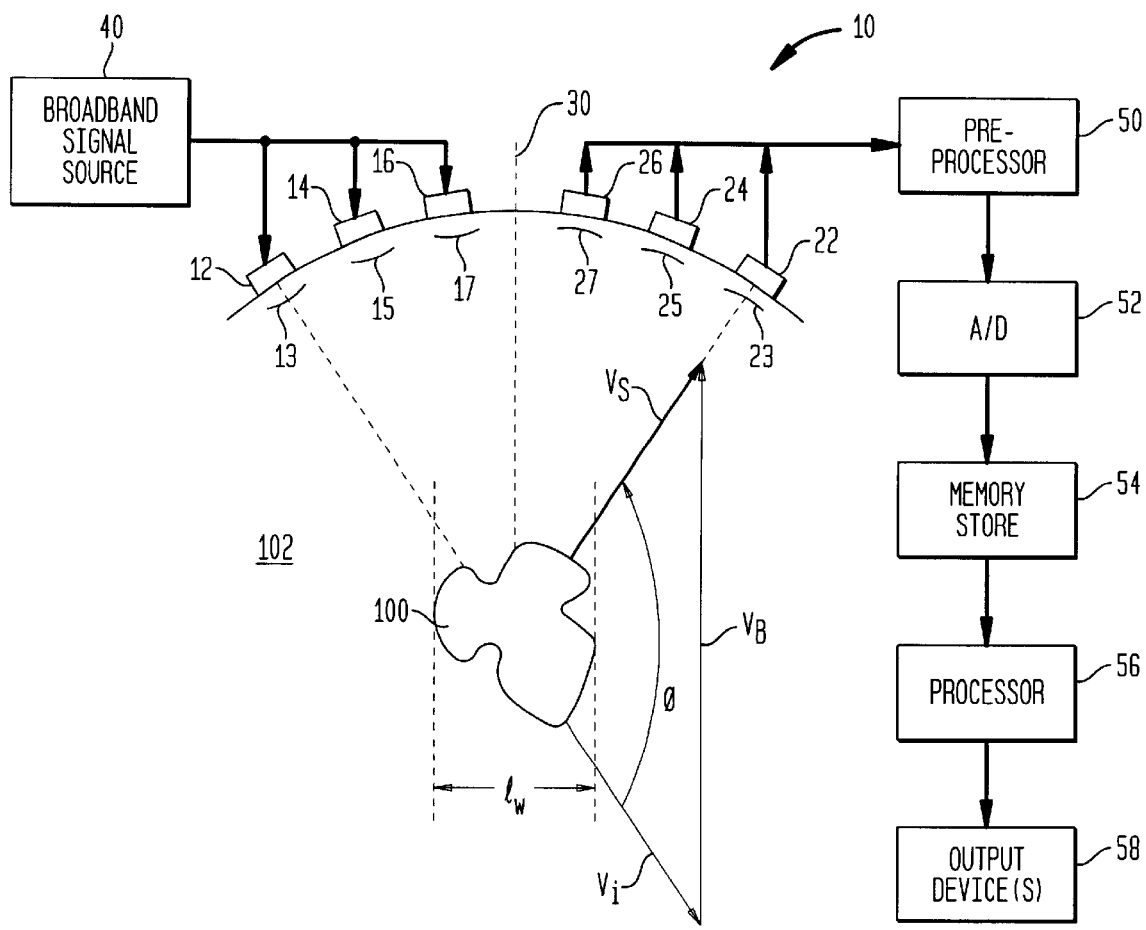
FIG. 1 is a schematic diagram of the system for carrying out the acoustic scattering technique for determining multiple feature variances in a medium in accordance with the present invention.

Referring now to the drawings, and more particularly to FIG. 1, a system for determining multiple features of a medium in accordance with the present invention is shown and referenced generally by numeral 10. By way of example, the present invention and system 10 will be described as a means and method for determining variations in temperature and salinity of a region 100 in the medium of water 102. However, the present invention could be used to determine variations in multiple features of any medium that transmits soundwaves. For example, the present invention can be used in medical diagnostic applications where it is desired to measure variations in sound speed and density of a human tissue medium.

System 10 typically has a plurality of acoustic sources 12, 14, 16 (e.g., transducers) and a corresponding plurality of acoustic receivers 22, 24, 26 positioned at mirror-imaged locations relative to a datum 30 indicative of a selected axis or direction in which acoustic scattering will be measured. Each mirror-imaged pair of acoustic sources/receiver (e.g., source 12/receiver 22, source 14/receiver 24 and source 16/receiver 26) define a channel as it will be referred to herein. Although system 10 is depicted with three channels, more or less channels could be used. For example, a single channel (i.e., single acoustic source and receiver) could be used in certain applications. Alternatively, the source/receiver hardware for a single channel could be moved to multiple locations thereby synthetically creating the effect of multiple channels.

Each of sources 12, 14, 16 is positioned to direct acoustic energy towards region 100 in a medium such as water 102 in the illustrative embodiment. Sources 12, 14, 16 are positioned so that each ensonifies the same volume of region 100 for purposes of acoustic scattering. Accordingly, sources 12, 14, 16 can be placed on the arc of a circle as shown. Sources 12, 14, 16 could also be placed along a line or otherwise, provided they could be operated so that each source ensonifies the same volume of region 100.

Coupled to each of acoustic sources 12, 14, 16 is a broadband signal source 40 capable of exciting each of sources 12, 14, 16 individually to emit a broadband ultrasonic pulse towards region 100 resulting in respective traveling acoustic waves 13, 15, 17. As used herein, "broadband" means a bandwidth of approximately 50% of the center frequency of the acoustic (transducer) sources 12, 14, 16. Each of sources 12, 14, 16 is excited at a unique time such that the time span between excitations is sufficient for the channel's corresponding acoustic receiver to make its acoustic scattering measurement and for any transients to die off. Such broadband signal sources and timing schemes are well known in the art and need not be described further herein.

Each of acoustic receivers 22, 24, 26 provides its received output in the form of a continuous electric signal to a processing system that includes a pre-processor 50, an analog-to-digital (A/D) converter 52, a memory store 54, a processor 56 and one or more output device(s) 58. Since each of acoustic receivers 22, 24, 26 is in a mirror-imaged position relative to corresponding acoustic sources 12, 14, 16, each of receivers 22, 24, 26 sees the same volume of region 100 for purposes of measuring acoustic scatter therefrom.

As will be explained in greater detail below, pre-processor 50 provides a variety of acoustic processing devices/functions for processing the continuous signal output of acoustic receivers 22, 24, 26 prior to the conversion thereof to digital signal representations by A/D converter 52. Memory store 54 stores the digital signals. Processor 56 processes the stored digital signals at the prescribed time to generate an estimate of, in this case, temperature and salinity variations that can be output to device(s) 58, e.g., display, printer, synthetic voice device, etc.

Figure 2:
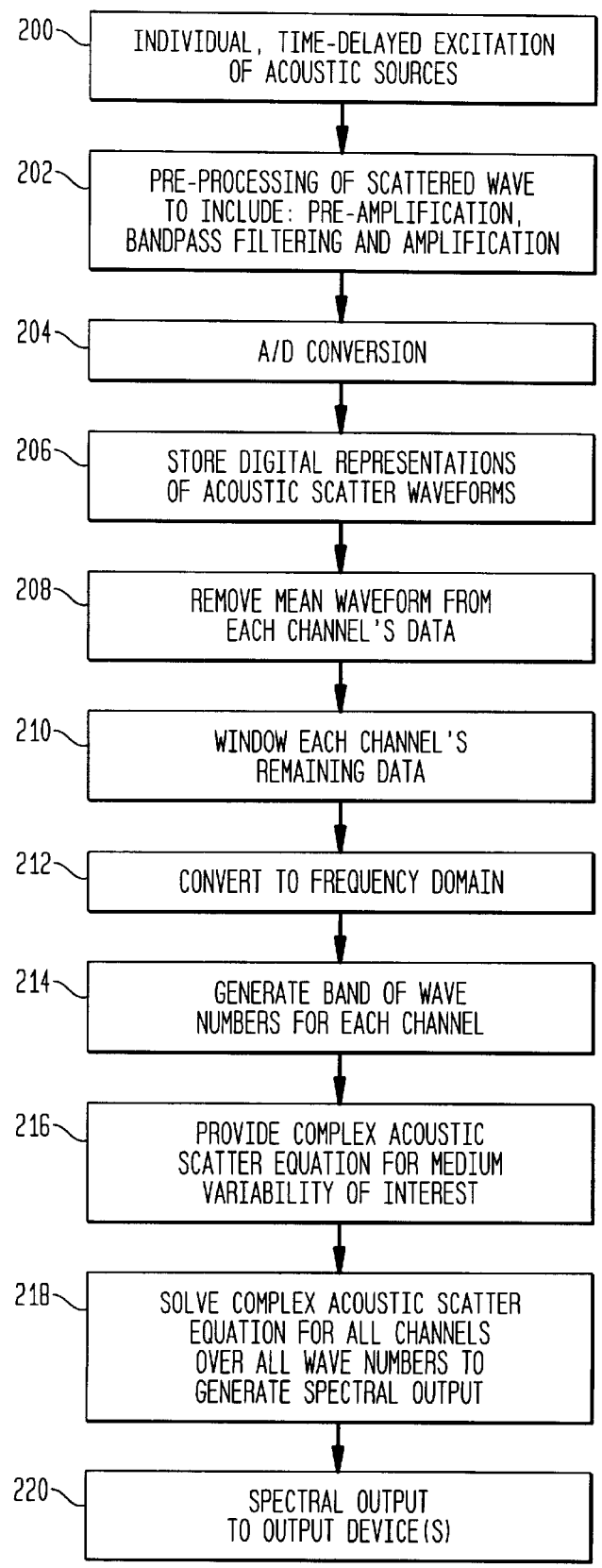
FIG. 2 is a flow chart of the method of the present invention.

Referring additionally to the flow chart in FIG. 2, the method of the present invention will now be described. At step 200, acoustic sources 12, 14, 16 are individually excited in a time-delayed fashion to emit a broadband acoustic pulse into water 102 so that acoustic waves 13, 15, 17 are directed towards region 100 as described above. Using far-field weak scattering theory, it can be assumed that waves 13, 15, 17 are planar and that multiple scattering can be ignored. As each of acoustic waves 13, 15, 17 is incident on region 100, corresponding acoustic scatter waves 23, 25, 27 are produced and thereafter detected by corresponding acoustic receivers 22, 24, 26.

Since the data collection portion of the present invention is the same for each channel, the details of data collection will only be described for one channel, i.e., acoustic source 12/receiver 22. As mentioned above, the incidence of acoustic wave 13 results in scattered wave 23 being detected at acoustic receiver 22. Geometrically, as illustrated in FIG. 1, acoustic wave 13 travels in the direction of an incident wave vector $V_i$ while scattered wave 23 detected by acoustic receiver 22 travels in the direction of a scattered wave vector $V_s$. The magnitude of $V_i$ and $V_s$ are equal to one another due to the conservation of momentum. This means that the wavelength of sound that is scattered is equal to the wavelength of sound that is incident upon the scattering region, i.e., region 100. This fact combined with mirror-image positioning of source 12/receiver 22 about selected scattering direction 30 means that a Bragg scattering wave vector $V_B$ (i.e., the difference vector between $V_i$ and $V_s$) is parallel to selected scattering direction 30. This will be true for each channel of system 10. The angle θ between $V_i$ and $V_s$ is known as the acoustic scattering angle, which will be unique for each channel.

Acoustic receiver 22 detects scattered wave 23 and presents a continuous signal representation thereof to pre-processor 50. The processes typically carried out by pre-processor 50 are standard acoustic signal processes and can include pre-amplification, bandpass filtering and further amplification as indicated at step 202. Analog-to-digital (A/D) conversion of the pre-processed signals is carried out by A/D converter 52 as indicated at step 204. The digitized waveform of acoustic scatter wave 23 is stored in memory store 54 as indicated at step 206. The process described by steps 200–206 is repeated for each channel. Additionally, steps 200–206 can be repeated for all channels a number of times, i.e., over a selected period of time, so that variations of a medium's features with respect to time can be stored for immediate or later evaluation.

Processor 56 carries out steps 208 as will be explained below. Similar to the data collection portion of the present invention, part of the processing carried out by processor 56 is the same for each channel. Specifically, steps 208–214 are the same for each channel. Accordingly, the details of these steps will only be described or one channel, i.e., acoustic source 12/receiver 22.

For the illustrative example, it will be assumed that data collection is repeated for all channels a number of times so that a number of digitized waveforms for each channel are available. At step 208, the mean waveform of the stored digitized waveforms is removed for each channel. The remaining digitized waveforms are windowed in time (at step 210) with a Gaussian function weighted to a mean profile of the magnitude of the mean of the scattered waves. This enhances the signal-to-noise ratio and eliminates any possible aliasing. The windowed, digitized waveforms are then converted to the frequency domain at step 212 by means of a fast Fourier transform (FFT). The resulting spectral waveforms associated with the channel defined by source 12/receiver 22 have a corresponding band of Bragg wave numbers K. Specifically, the Bragg wave number K is a function of the acoustic wave number k of acoustic wave 13 and the scattering angle θ for that channel. That is, as is known in the art, $$K = 2k \sin \theta \qquad (1)$$

In the present invention, the multiple sets of broadband Bragg wave numbers associated with the plurality of channels have two purposes. The first purpose is to more fully resolve the scattering feature(s) and the second is to provide spectral continuity in wave number space from channel to channel. The Bragg wave numbers associated with each channel are used to form a universal set of Bragg wave numbers. This is accomplished by generating a set of Bragg wave numbers that span from the minimum to the maximum values of the entire sets of Bragg wave numbers associated with all channels. The acoustic spectra associated with each channel are then fitted in a least squares sense to the universal set of Bragg wave numbers. These steps are referenced generally at step 214.

Once steps 208–214 have been carried out for each of the channels, a non-linear system of j equations and four unknowns can be expressed in terms of the acoustic scatter due to variations in a medium where j indicates the number of channels, e.g., j is equal to three for system 10. This step is indicated generally at step 216. More specifically, for the illustrative example of far-field weak scattering in water due to variations in temperature and salinity using transducers modeled as baffled pistons and referenced to the 10 dB down point, and locating the scattering volume in the transition zone between the first near-field null referenced to infinity and the classical far-field limit, the complex acoustic scatter $p_s$ is $$\frac{5.4 k p_i l_w}{4\pi a}(a_T T(K) + a_s S(K)) \tag{2}$$

where $p_i$ is a complex incident acoustic field associated with the broadband acoustic pulse emitted from, in this case, acoustic source 12, $l_w$ is a width of the volume of the acoustic scattered wave detected by, in this case, acoustic receiver 22 where $l_w$ is measured perpendicular to scattering direction 30, a is a radius of acoustic source 12, $a_T$ is equal to $2\alpha+\beta(1-\cos\theta)$ where $\alpha=2\times10^{-3}$ C.$^{-1}$, $\beta=-2\times10^{-4}$ C.$^{-1}$, T(K) is a complex Fourier transform of a temperature difference field aligned with scattering direction 30 as a function of K, $a_S$ is equal to $2\chi+\delta(1-\cos\theta)$ where $\chi=8\times10^{-4}$ psu$^{-1}$ (where "psu" is "practical salinity units") and $\delta=8\times10^{-4}$ psu$^{-1}$, and S(K) is a complex Fourier transform of a salinity difference field aligned with scattering direction 30 as a function of K.

The fundamental equation for complex acoustic scatter from medium variability from which equation (2) was derived is described in "Theoretical Acoustics," by Morse et al., Princeton University Press, 1968, at page 413, equation 8.1.20. It is this fundamental equation that can be used to derive other complex acoustic scatter relationships for other medium variabilities such as sound speed and density in human tissue as will be described further below.

Equation (2) can be manipulated into a more convenient form given by $$|b|^2 \equiv \left|\frac{4\pi a p_s}{5.4 k p_i l_w}\right|^2 = a_T^2 T^2 + a_S^2 S^2 + 2 a_T a_S T S \cos\Delta \tag{3}$$

where

T is the magnitude of the complex function T(K),

S is the magnitude of the complex function S(K), and

Δφ represents the change in phase between the temperature and salinity spectra

For the illustrative example, Δφ is zero because temperature and salinity variations are being considered for the same region, i.e., region 100.

A resulting set of j by 2 system of equations results when considering all j channels of system 10. Solving the set of equations at step 218 for all channels can be accomplished using a variety of techniques such as the well-known Newton's method which is described in detail in "Newton's Method: Numerical Methods That Work," Forman S. Acton, The Mathematical Association of America, Washington, D.C., 1990, p. 367–369. Briefly, Newton's method is a root finding method that iterates over a gradient field until the solution converges. The solution in the present invention is a matrix solution Δ that converges when $$\Delta = -G^{-1} F \tag{4}$$

where G is a j by 2 matrix $\{G_j\}$ and F is a j×1 vector $\{F_j\}$, and where, in the illustrated example, the j-th row of the matrix G has the two columns of elements as follows:

$$\{G_j\} = \{-2a_{Tj}^2 T - 2a_{Tj} a_{sj} S - 2a_{Sj}^2 S - 2a_{Tj} a_{Sj} T\} \tag{5}$$

and $$\{F_j\} = \{|b|^2 - a_{Tj}^2 T^2 - a_{Sj}^2 S^2 - 2a_{Tj} a_{Sj} T S\} \tag{6}$$

To solve for Δ, Singular Value Decomposition (SVD) of matrix G can be used where $G = U \Sigma V_1$. Solving equations by SVD is described in detail in "Numerical Recipes (Fortran Version)," Press et al., Cambridge University Press, Cambridge, Mass., 1990, p. 52–60. Since this is an overdetermined system of equations, the matrix solution to Δ is implemented as follows $$\Delta = -V_1 \begin{bmatrix} \frac{1}{\Sigma(1,1)} & 0 & 0 \\ 0 & \frac{1}{\Sigma(2,2)} & 0 \end{bmatrix} U' F \tag{7}$$

As a result of solution convergence, the temperature and salinity difference spectra at given Bragg wave number K are determined. Step 218 includes the repeating of the solution convergence process for all available Bragg wave numbers K. The ultimate result is a spectral output of temperature and salinity as a function of Bragg wave number K. The spectral output can be output to device 58 at step 220.

The advantages of the present invention are numerous. Multiple features of a medium can be determined non-invasively and simultaneously. Feature variances with respect to time can be used to monitor changing conditions. The present invention can be applied to a variety of media such as water and human tissue.

The present invention combines expanded information (bandwidth) that can be obtained from the measurements made at multiple scattering angles with mathematically-established techniques used to solve systems of nonlinear equations. This is possible because each of the features (e.g., temperature and salinity) have slightly different angular scattering properties. Because these differences are so small and often close to system noise levels, the expanded information obtained via broadband multi-static scattering has a smoothing effect when attempting to extract features from low signal-to-noise ratio type of signals.

Although the invention has been described relative to a specific embodiment thereof, there are numerous variations and modifications that will be readily apparent to those skilled in the art in light of the above teachings. For example, the present invention could be used to determine variations in sound speed and density of a human tissue medium. In such a case, the complex scatter $p_s$ is $$\frac{5.4 k p_i l_w}{4 \pi a}(a_c c(K) + a_\rho \rho(K)) \quad (8)$$

where $p_i$ is a complex incident acoustic field associated with the broadband acoustic pulse emitted from an acoustic source as described above, $l_w$ is a width of the volume of the acoustic scattered wave detected by a corresponding acoustic receiver as described above, a is a radius of the acoustic source, $a_c$ is equal to $2/c_0$ where $c_0$ is the ambient sound speed in the surrounding medium, c(K) is a complex Fourier transform of a sound speed difference field aligned with the scattering direction as a function of K as described above, $a_\rho$ is equal to $(1-\cos \theta)/\rho$ where $_0\rho$ is the ambient density in the surrounding medium, and $\rho(K)$ is a complex Fourier transform of a density difference field aligned with the scattering direction as a function of K as described above.

It is therefore to be understood that, within the scope of the appended claims, the invention may be practiced other than as specifically described.

What is claimed as new and desired to be secured by Letters Patent of the United States is:

1. A method for determining multiple feature variances in a medium, comprising the steps of:

selecting a scattering direction relative to a region of interest in a medium;

positioning acoustic sources on one side of said scattering direction;

positioning acoustic receivers on an opposite side of said scattering direction wherein, for each of said acoustic sources, there is a corresponding one of said acoustic receivers located at a mirror-imaged position relative to said scattering direction such that Bragg scattering wave vector associated with each of said acoustic sources and its corresponding one of said acoustic receivers is parallel to said scattering direction;

operating each of said acoustic sources at a unique time to direct a broadband ultrasonic pulse at said region of interest in a first direction herein an acoustic scattered wave reflects from said region of interest in a second direction;

detecting each said acoustic scattered wave as a waveform at said corresponding one of said acoustic receivers;

digitizing each said waveform to form a digital waveform;

converting each said digital waveform to the frequency domain to form a spectral waveform;

determining a band of Bragg wave numbers for each said spectral waveform; and determining variations in multiple features of said medium as a function of each said band of Bragg wave numbers.

2. A method according to claim 1, wherein said medium is water, and wherein said multiple features comprise temperature and salinity of the water.

3. A method according to claim 1, wherein said medium is human tissue, and wherein said multiple features comprise sound speed and density of the human tissue.

4. A method according to claim 1, wherein said steps of operating and detecting are repeated to generate a plurality of waveforms associated with each of said acoustic receivers.

5. A method according to claim 4, further comprising the step of removing a mean waveform from said plurality of waveforms associated with each of said acoustic receivers prior to said step of converting.

6. A method according to claim 2, wherein said steps of operating and detecting are repeated to generate a plurality of waveforms associated with each of said acoustic receivers.

7. A method according to claim 6, further comprising the step of removing a mean waveform from said plurality of waveforms associated with each of said acoustic receivers prior to said step of converting, wherein said step of converting forms a mean spectral waveform associated with each of said acoustic receivers.

8. A method according to claim 7, wherein said step of determining variations comprise the steps of:

providing an equation in indicative of complex acoustic scatter in the form of $$\frac{5.4 k p_i l_w}{4 \pi a}(a_T T(K) + a_S S(K))$$

where k is the acoustic wave number of said broadband acoustic pulse, $p_i$ is a complex incident acoustic field associated with said broadband acoustic pulse from one of said acoustic sources, $l_w$ is a width of the volume of said acoustic scattered wave detected by said corresponding one of said acoustic receivers measured perpendicular to said scattering direction, a is a radius of said one of said acoustic sources, $a_T$ is equal to $2\alpha + \beta(1-\cos \theta)$ where $\alpha = 2 \times 10^{-3 \circ}$ $C.^{-1}$, $\beta = -2 \times 10^{-4 \circ}$ $C.^{-1}$, and $\theta$ is a scattering angle defined as the angle between said first direction and said second direction associated with said one of said acoustic sources, T(K) is a complex Fourier transform of a temperature difference field aligned with said scattering direction as a function of K, K is said band of Bragg wave numbers associated with said scattering angle $\theta$, $a_s$ is equal to $2\chi + \delta(1-\cos \theta)$ where $\chi = 8 \times 10^{-4}$ $psu^{-1}$ and $\delta = 8 \times 10^{-4}$ $psu^{-1}$, and S is a complex Fourier transform of a salinity difference field aligned with said scattering direction as a function of K; and solving said equation over each said band of Bragg wave numbers to generate a spectral estimate of temperature and salinity variations as a function of said band of Bragg wave numbers.

9. A method according to claim 3, wherein said steps of operating and detecting are repeated to generate a plurality of waveforms associated with each of said acoustic receivers.

10. A method according to claim 9, further comprising the step of removing a mean waveform from said plurality of waveforms associated with each of said acoustic receivers prior to said step of converting, wherein said step of converting forms a mean spectral waveform associated with each of said acoustic receivers.

11. A method according to claim 10, wherein said step of determining variations comprise the steps of:

provide an equation indicative of complex acoustic scatter in the form of $$\frac{5.4kp_i l_w}{4\pi a}(a_c c(K) + a_\rho \rho(K))$$

where k is the acoustic wave number of said broadband acoustic pulse, $p_i$ is a complex incident acoustic field associated with said broadband acoustic pulse from one of said acoustic sources, $l_w$ is a width of the volume of said acoustic scattered wave detected by said corresponding one of said acoustic receivers measured perpendicular to said scattering direction, a is a radius of said one of said acoustic sources, $a_c$ is equal to $2/c_0$ where $c_0$ is an ambient sound speed in the medium, c(K) is a complex Fourier transform of a sound speed difference field aligned with said scattering direction as a function of K, K is said band of Bragg wave numbers associated with said scattering angle $\theta$, $a_\rho$ is equal to $(1-\cos\theta)/_0\rho$ where $_0\rho$ is an ambient density in the medium, and $\rho(K)$ is a complex Fourier transform of a density difference field aligned with said scattering direction as a function of K; and solving said equation over each said band of Bragg wave numbers to generate a spectral estimate of sound speed and density variations as a function of said band of Bragg wave numbers.

12. A method for determining multiple feature variances in a medium, comprising the steps of:

selecting a scattering direction relative to a region of interest in a medium, said region of interest having a width measured perpendicular to said scattering direction;

positioning acoustic sources on one side of said scattering direction;

positioning acoustic receivers on an opposite side of said scattering direction wherein a plurality of channels are defined with each of said plurality of channels including one of said acoustic sources and one of said acoustic receivers located at a mirror-imaged position relative to said scattering direction such that a Bragg scattering wave vector associated with each of said plurality of channels is parallel to said scattering direction;

operating each of said plurality of channels at a unique time to direct a broadband ultrasonic pulse at said region of interest in a first direction wherein an acoustic scattered wave reflects from said region of interest in a second direction and is detected as a waveform;

digitizing each said waveform to form a plurality of digital waveforms;

removing a mean waveform from each of said plurality of waveforms to define a reduced plurality of digital waveforms;

converting each of said reduced plurality of digital waveforms to the frequency domain wherein a corresponding plurality of spectral waveforms are generated;

constructing a band of Bragg wave numbers for each of said plurality of spectral waveforms; and determining variations in multiple features of said medium as a function of said band of Bragg wave numbers for each of said plurality of spectral waveforms.

13. A method according to claim 12, wherein said medium is water, and wherein said multiple features comprise temperature and salinity of the water.

14. A method according to claim 12, wherein said medium is human tissue, and wherein said multiple features comprise sound speed and density of the human tissue.

15. A method according to claim 13, wherein said step of determining variations comprises the steps of:

providing a first equation indicative of complex acoustic scatter $p_s$ in the form of $$\frac{5.4kp_i l_w}{4\pi a}(a_T T(K) + a_S S(K))$$

where k is the acoustic wave number of said broadband acoustic pulse, $p_i$ is a complex incident acoustic field associated with said broadband acoustic pulse for one of said plurality of channels, $l_w$ is a width of the volume of said acoustic scattered wave detected by said one of said plurality of channels measured perpendicular to said scattering direction, a is a radius of one of said acoustic sources from said one of said plurality of channels, $a_T$ is equal to $2\alpha+\beta(1-\cos\theta)$ where $\alpha=2\times10^{-3\circ}$ C.$^{-1}$, $\beta=-2\times10^{-4\circ}$ C.$^{-1}$, and $\theta$ is a scattering angle defined as the angle between said first direction and said second direction for each of said one of said plurality of channels, T(K) is a complex Fourier transform of a temperature difference field aligned with said scattering direction as a function of K, K is said band of Bragg wave numbers associated with said one of said plurality of channels, $a_S$ is equal to $2\chi+\delta(1-\cos\theta)$ where $\chi=8\times10^{-4}$ psu$^{-1}$ and $\delta=8\times10^{-4}$ psu$^{-1}$, and S(K) is a complex Fourier transform of a salinity difference field aligned with said scattering direction as a function of K;

manipulating said first equation into the form of a second equation defined as $$|b|^2 = a_T^2 T^2 + a_S^2 S^2 + 2a_T a_S TS$$

where $$b \equiv \frac{4\pi a p_s}{5.4kp_i l_w},$$

T is the magnitude of said complex Fourier transform T(K), and

S is the magnitude of said complex Fourier transform S(K); and solving said second equation over said band of wave numbers for each of said plurality of channels to generate a spectral estimate of temperature and salinity variations as a function of said band of Bragg wave numbers.

16. A method according to claim 14, wherein said step of determining variations comprises the steps of:

providing a first equation indicative of complex acoustic scatter $p_s$ in the form of $$\frac{5.4 k p_i l_w}{4\pi a}(a_c c(K) + a_\rho \rho(K))$$

where k is the acoustic wave number of said broadband acoustic pulse, $p_i$ is a complex incident acoustic field associated with said broadband acoustic pulse from one of said acoustic sources, $l_w$ is a width of the volume of said acoustic scattered wave detected by said corresponding one of said acoustic receivers measured perpendicular to said scattering direction, a is a radius of said one of said acoustic sources, $a_c$ is equal to $2/c_0$ where $c_0$ is an ambient sound speed in the medium, c(K) is a complex Fourier transform of a sound speed difference field aligned with said scattering direction as a function of K, K is said band of Bragg wave numbers associated with said scattering angle θ, $a_\rho$ is equal to $(1-\cos\theta)/_0\rho$ where $_0\rho$ is an ambient density in the medium, and ρ(K) is a complex Fourier transform of a density difference field aligned with said scattering direction as a function of K;

manipulating said first equation into the form of a second equation defined as $$|b|^2 = a_c^2 c^2 + a_\rho^2 \rho^2 + 2 a_c a_\rho c \rho$$

where $$b \equiv \frac{4\pi a p_s}{5.4 k p_i l_w},$$

c is the magnitude of said complex Fourier transform c(K), and

ρ is the magnitude of said complex Fourier transform p(K); and solving said second equation over said band of wave numbers for each of said plurality of channels to generate a spectral estimate of sound speed and density variations as a function of said band of Bragg wave numbers.

* * * * *